United States Patent
Damer et al.

(10) Patent No.: US 7,343,782 B2
(45) Date of Patent: Mar. 18, 2008

(54) SYSTEM AND METHOD FOR PERFORMING QUANTIFIABLE RELEASE SPORE TESTING ON BIOAEROSOL DETECTION TECHNOLOGIES

(75) Inventors: Kenneth S. Damer, Parkville, MD (US); Edmond G. Radcliff, Laurel, MD (US)

(73) Assignee: Northrop Grumman Corporation, Los Angeles, CA (US)

( * ) Notice: Subject to any disclaimer, the term of this patent is extended or adjusted under 35 U.S.C. 154(b) by 137 days.

(21) Appl. No.: 11/400,237

(22) Filed: Apr. 10, 2006

(65) Prior Publication Data

US 2007/0234777 A1    Oct. 11, 2007

(51) Int. Cl.
  *G01D 18/00* (2006.01)
  *G01N 21/85* (2006.01)

(52) U.S. Cl. .................. 73/31.03; 73/28.01; 73/31.02; 73/31.05

(58) Field of Classification Search ................. 73/1.01, 73/1.02, 1.24, 31.02, 28.01, 31.05
See application file for complete search history.

(56) References Cited

U.S. PATENT DOCUMENTS

| | | | |
|---|---|---|---|
| 4,004,882 A * | 1/1977 | Byrne et al. ................. | 422/83 |
| 4,213,325 A | 7/1980 | Tumanov et al. | |
| 4,436,699 A * | 3/1984 | Narato et al. ................. | 422/73 |
| 5,150,036 A | 9/1992 | Pourprix | |
| 5,502,998 A | 4/1996 | Miller et al. | |
| 5,604,295 A * | 2/1997 | Robinson .................... | 73/1.03 |
| 5,747,667 A * | 5/1998 | Sadar ......................... | 73/1.02 |
| 5,895,922 A | 4/1999 | Ho | |
| 5,918,254 A | 6/1999 | Bottiger et al. | |
| 6,498,041 B1 | 12/2002 | Tabacco et al. | |
| 6,532,067 B1 | 3/2003 | Chang et al. | |
| 6,573,836 B1 | 6/2003 | Gitis et al. | |
| 6,599,715 B1 | 7/2003 | Vanderberg et al. | |
| 6,672,129 B1 | 1/2004 | Frederickson et al. | |
| 6,672,133 B1 | 1/2004 | Maswadeh et al. | |
| 6,694,796 B2 * | 2/2004 | Juneau et al. ................ | 73/1.03 |
| 6,711,939 B2 | 3/2004 | Megerle et al. | |
| 6,765,668 B2 | 7/2004 | Gardner, Jr. et al. | |
| 6,838,292 B1 | 1/2005 | Rajan et al. | |
| 6,865,926 B2 | 3/2005 | O'Brien et al. | |
| 2003/0106362 A1 | 6/2003 | Megerle | |
| 2003/0145664 A1 | 8/2003 | Schwarz et al. | |
| 2004/0010379 A1 | 1/2004 | Craig et al. | |
| 2004/0020264 A1 | 2/2004 | Megerle | |
| 2004/0024539 A1 | 2/2004 | Gard et al. | |
| 2004/0063197 A1 | 4/2004 | Tilles et al. | |

(Continued)

*Primary Examiner*—Daniel S. Larkin
*Assistant Examiner*—David A. Rogers
(74) *Attorney, Agent, or Firm*—Rothwell, Figg, Ernst & Manbeck, PC

(57) ABSTRACT

A system for testing devices for detecting airborne particulate matter generates a first airflow and a second airflow. The second airflow is filtered to remove ambient airborne particulate matter from the second airflow, and particulate matter to be detected is aerosolized and introduced into the second airflow. The second airflow is sampled by an optical particle counter to determine an amount of particulate matter released into the second airflow. The first and second airflows are combined, and the combined airflows are sampled by one or more detecting devices to be tested. Detection results of the tested detecting devices are compared with the amount of particulate matter released into the second airflow as determined by the optical particle counter to assess the accuracy and functionality of the detecting devices.

13 Claims, 1 Drawing Sheet

U.S. PATENT DOCUMENTS

| | | |
|---|---|---|
| 2004/0075049 A1 | 4/2004 | Stowers et al. |
| 2004/0125371 A1 | 7/2004 | Chang et al. |
| 2004/0189989 A1 | 9/2004 | Gardner, Jr. et al. |
| 2004/0220753 A1 | 11/2004 | Tabe |
| 2004/0232052 A1 | 11/2004 | Call et al. |
| 2005/0109128 A1* | 5/2005 | Pasquereau et al. ..... 73/863.21 |

* cited by examiner

SYSTEM AND METHOD FOR PERFORMING QUANTIFIABLE RELEASE SPORE TESTING ON BIOAEROSOL DETECTION TECHNOLOGIES

FIELD OF THE INVENTION

The invention is in the field of systems and methods for testing the accuracy and effectiveness of bioaerosol detection technologies.

BACKGROUND OF THE INVENTION

Biohazard Detection Systems (BDS) have been developed for detecting biohazardous airborne particulate matter in environments that are susceptible to infiltration by such matter. A particular application of BDS is a threat detection system for postal processing machinery capable of detecting low-level releases of anthrax. A typical BDS cabinet used in conjunction with postal equipment contains within it a blower module drawing an airflow (e.g., 400 liters per minute (LPM)). The blower is used to draw air from a collection hood/manifold installed on standard mail processing equipment, or from the ambient environment.

Future hazardous material detection systems will include the ability to detect various other biological and toxic aerosol threats.

Historically, the majority of acceptance/qualification testing conducted on a typical BDS unit has required the use of operating the mail processing equipment complete with the air collection equipment. A carrier "hot" envelope that has been loaded with a weighed quantity of the hazardous material to be detected is then processed through the equipment along with other "cold" envelopes to generate background dust and particulates. Particulate emissions generated are then collected by the hood/manifold and are drawn into the BDS unit. As this is a highly dynamic system, there is no way to control the amount of target material released from the envelope for any given test, as the quantity of the release is only partially dependent on the weight of the material carried in the hot envelope. Furthermore, this testing, although adequate to meet the qualification needs of current BDS units, is limited, both in its ability to test the BDS cabinet for use in non-postal applications and in its ability to evaluate new detection technologies for use in chemical/biological detection applications.

Thus, a need exists for a system for testing and qualifying particulate detection devices that is accurate and flexible in its application to a variety of types of particulate matter for use in a variety of environments with different background clutter.

SUMMARY OF THE INVENTION

An object of the present invention is to provide a system and method of generating an aerosol release of particulate matter, and combine it with the means to accurately measure that release and then allow for the release to be injected into an existing airflow (which may contain other background particulates) that is being monitored by the device being tested.

Aspects of the invention are embodied in a system for testing a device for detecting the presence of airborne particulate matter. The system includes a primary airflow conduit and a secondary airflow conduit. A filter removes ambient particulate matter from the secondary airflow, and a particulate aerosol generator aerosolizes an amount of target particulate matter that is released into the secondary airflow. A particulate measuring apparatus samples the secondary airflow and measures the amount of particulate matter released into the secondary airflow. The primary and secondary airflows are combined, and the device for detecting the presence of airborne particulate matter is tested by positioning it operatively with respect to the combined primary and secondary airflows so that it can detect the airborne particulate matter that was initially released into the secondary airflow and is now present in the combined airflow, along with other potential particulates from the primary airflow.

Aspects of the invention are further embodied in a method for testing a device for detecting the presence of airborne particulate matter. The method includes generating a first airflow, generating a second airflow, and filtering the second airflow to remove ambient particulate matter from the second airflow. An amount of the particulate material to be detected by the device for detecting is aerosolized and injected into the second airflow. The second airflow is sampled to quantify the particulate material injected into the second airflow of air. The first and second airflows are combined to create a combined airflow, and the combined airflow is measured with the device for detecting to be tested.

Further details and aspects of the invention will be appreciated by reference to the following detailed description with reference to the accompanying drawing and by reference to the appended claims.

DETAILED DESCRIPTION OF THE PREFERRED EMBODIMENT

Figure 1:
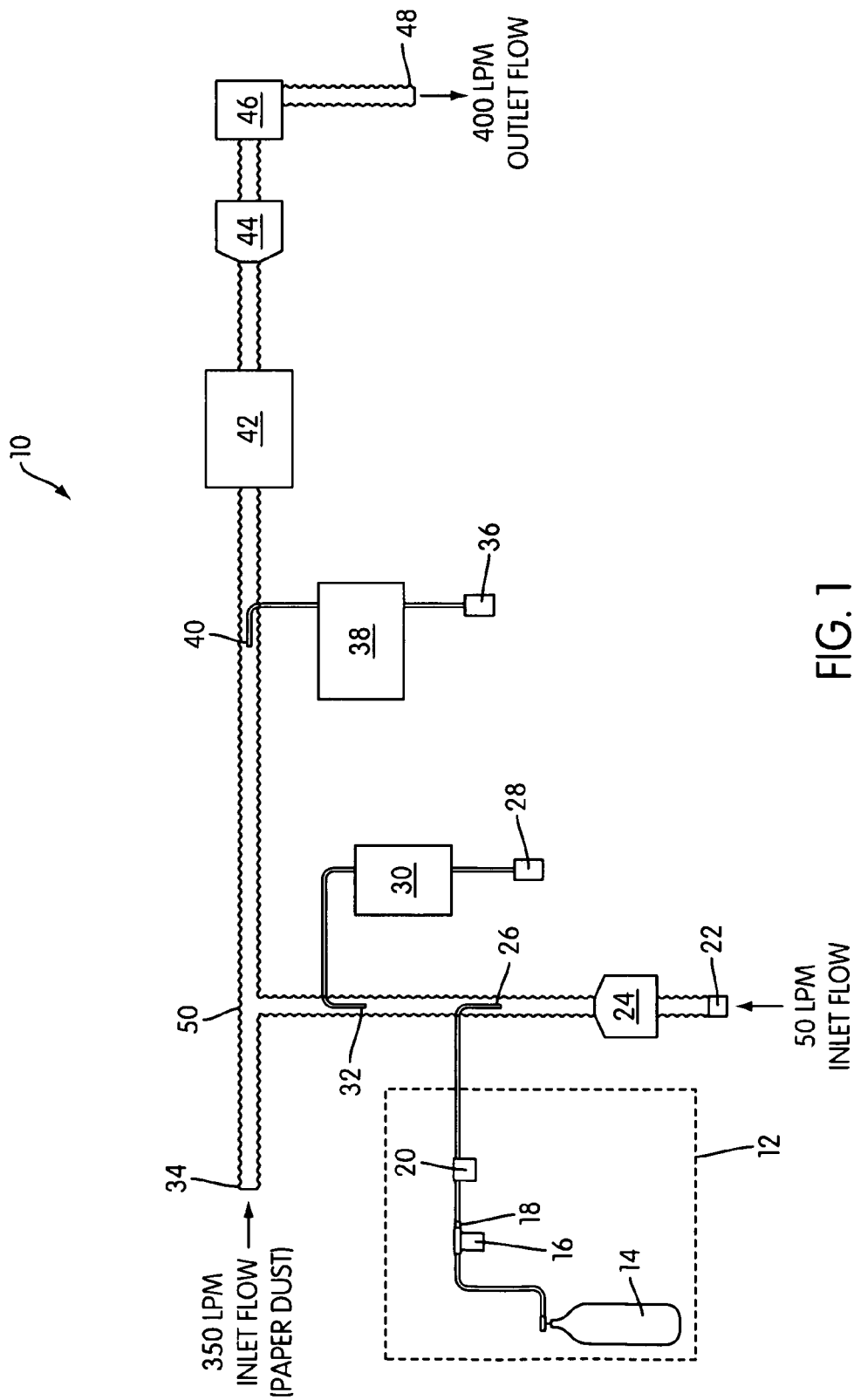
FIG. 1 is a schematic view of a system embodying aspects of the present invention.

A system for qualifying particulate detection devices and embodying aspects of the present invention is designated generally by reference number 10 in FIG. 1. FIG. 1 is a schematic view of such a system. In general, the system generates an airflow and introduces a measured quantity of target particulate matter into the airflow. One or more particulate detection devices then sample the airflow into which the particulate matter has been introduced, and the output of the particulate detection devices is compared to the amount of particulate matter originally introduced into the airflow to assess the accuracy and functionality of the particulate detection devices. More specifically, a blower 46 draws a primary airflow into the primary flow inlet 34 and a secondary airflow into the secondary flow inlet 22. A measurable quantity of particulate matter is generated by the aerosol particle generator 12 and introduced into the airflow at 26. The secondary airflow is preferably filtered by the filter 24 to ensure that the only particulate matter in the secondary airflow is that which is released at 26. The amount of particulate matter introduced into the secondary airflow is measured by device 40. The primary and secondary airflows are then mixed at point 50, and the combined airflows are directed toward one or more particulate detection devices. In an exemplary system, the primary, secondary, and mixed airflows flow within a pipe, hose, duct, or other type of conduit.

Still more specifically, the primary airflow introduced as primary flow inlet 34 is preferably drawn from ambient operating conditions of the detection device being evaluated.

For example, for a detection device to be operated in a postal processing center, the device would be tested and air would be drawn from ambient conditions in the postal processing center, which may contain paper particulate matter floating in the air. Alternatively, ambient conditions can be artificially created to simulate the operational environment of the detection device. In the illustrated embodiment, air is drawn into the primary flow inlet 34 at a rate of 350 liters per minute (LPM). A secondary flow inlet is provided at 22 to draw ambient airflow at a preferred rate of 50 LPM. The secondary flow is drawn through a filter 24, for example, a HEPA filter, to remove ambient particles from the secondary airflow. A measurable quantity of a particulate substance is introduced into the secondary airflow at the particulate release point 26, which, in the illustrated embodiment, embodies a tube positioned within the secondary airflow. The released particulate matter is generated by the aerosol particle generator 12.

In the illustrated embodiment, the aerosol particle generator 12 includes a particle container 16 holding an amount of particulate material. For example, the particulate material may comprise spores of *Bacillus globigii* (Bg), a bio-aerosol commonly used as an anthrax stimulant. Other examples include *Erwinia Herbicola* (EH), a vegetative bacteria simulant, MS2 *Bacteriophage*, a virus simulant, and *Ovalbumin* (OV), a toxin simulant. In a preferred embodiment, means are provided to prevent the particulate matter from settling to the bottom of the container 16. For example, a magnetic stir bar, such as those commonly used in chemistry laboratories, may be placed inside the container 16. The container 16 includes a lid with ports for connecting in line with an airflow. One port is connected to a pressure source 14 which may comprise commercial grade nitrogen at a set pressure of 5-15 psi depending on the target size of the intended particulate release. Nitrogen prevents the introduction of moisture into the container that can lead to clumping of the particulate matter. Alternately, another type of inert gas, such as argon or neon, may also be used in place of nitrogen.

An electrically controlled valve 20 controls the timing of particulate injections, and a variably-sized orifice 18 between the valve 20 and the container 16 is used to further control the rate of discharge of the particulate released into the secondary airflow. Valve 20 may be a computer-controlled, solenoid-activated valve, and the size of orifice 18 may vary from 0.03 inches to 0.007 inches (other dimensions and ranges thereof are contemplated). The size of the particulate release can be varied by varying the length of time the valve 20 is open. In tests of the system, valve-open times varied from 10 milliseconds to 600 milliseconds. For larger releases, the valve 20 can be rapidly cycled on and off to allow the container 16 to remain pressurized.

The aerosol particle generator 12 shown and described will work for any dry powder capable of being aerosolized, but it is not necessarily the only means of generating an aerosol for use with the system. Essentially any system or apparatus that can generate an aerosol can be used. It is not critical that the aerosol release be consistent or predictable. Since the released aerosol is measured at counter 30, the amount of particulate flowing in the airflow will be known.

The aerosolized particulate matter is released into the secondary airflow by an injector at 26. A sampling probe 32 is positioned within the secondary air stream downstream of the particulate injector 26 separated far enough to allow complete mixing of the released aerosol within the secondary airflow. The sampling probe 32 is similar to a pitot tube, but its inner diameter is sized to sample the secondary airflow isokinetically to achieve an accurate representation of the concentration of particulate matter in the secondary airflow. Probe 32 draws a sample of the secondary airflow that is then analyzed by an optical particle counter (OPC) 30. In one embodiment, the OPC used is a MetOne Model 9012 6-channel particle counter with size channels of 0.7-1.0, 1.0-2.0, 2.0-3.0, 3.0-4.0, 4.0-5.0, and greater than 5.0 micrometers. Because the filter 24 prevents contamination of the secondary airflow by other particles (for example, at least particles having the same size as the target particles released from injector 26), the measurements provided by the OPC 30 reflect only particles released from the particle injector 26 without background interference. When combined with the use of isokinetic sampling, this data output from the OPC can then be used to determine a number of critical values: total aerosol particles released, peak number of aerosol particles released over a short segment of time (1 or more seconds), and size distribution of the release in the critical ranges between 0.7 micrometer and 5.0 micrometer. A simple example will illustrate: if it is assumed that the flow through the sampling probe 32 is 10% of the total secondary airflow, and the OPC 30 counts 10 particles (e.g., over a period of one second), because the airflow at the probe 32 is isokinetic, it can be assumed that the total number of particles flowing in the secondary airflow over the same period is approximately 100.

A HEPA filter 28 is provided at the exhaust of the OPC 30 to prevent environmental contamination from particles flowing through the OPC. If the particles removed from the secondary airflow by the sampling probe 32 are not re-injected into the secondary airflow, that amount of particles (i.e., the removed particles) should be subtracted from the total particles calculated for the secondary airflow.

The secondary airflow joins the primary airflow at 50 and preferably at an angle interface sufficient to create turbulence that will help ensure proper mixing of the primary airflow with the aerosolized particulate contained in the secondary airflow. From this junction, the airflow is now at a target flow rate of 400 LPM (note that the flow rates shown in FIG. 1 and described herein are merely exemplary) and is now ready for testing/analysis/sampling by the detection devices that are being tested.

Such devices may sample only a portion of the total flow, such as device 38 having an isokinetic sampling probe of 40 extending into the combined flow. Detection device 38 preferably includes a HEPA filter 36 to prevent environmental contamination by particulate matter flowing through the device 38. Alternatively, or in addition, the entire combined flow may be processed and analyzed such as by device 42 through which the entire flow is directed. The readings from devices 38 and/or 40 are correlated with the measured amount of target particulate to assess the effectiveness or accuracy of the devices. Some particulate detection devices respond to a specific total dosage of the target particulate, and other devices respond to a particular total concentration of the target particulate. Either type of device can be qualified, since an expected total dosage or an expected concentration can be determined from the measurements of the counter 30.

The HEPA filter 44 near the exhaust end of the system prevents particulate from being released back into the local environment. The flow is drawn through the blower 46 (which can be omitted if the device 42 being tested generates its own airflow) and is exhausted through the exhaust port 48.

The system described allows for the functionality and sensitivity testing of a wide range of detection devices: optical triggers, bio-fluorescent analysis, ion-mobility/mass-spectrometry, and virtually any other chemical/biological detection system that draws its sample from the air.

The foregoing description represents a presently preferred embodiment of the invention and is not intended to be limiting of the scope of the invention.

What is claimed is:

1. A system for testing a device for detecting the presence of airborne particulate matter comprising:
   a primary airflow conduit constructed and arranged to generate a primary airflow;
   a secondary airflow conduit constructed and arranged to generate a secondary airflow;
   a filter operatively positioned with respect to the secondary airflow to remove ambient particulate matter from the secondary airflow;
   a particulate aerosol generator constructed and arranged to generate an amount of airborne particulate matter and to release the generated airborne particulate matter into the filtered secondary airflow;
   an apparatus for measuring the amount of airborne particulate matter released into the secondary airflow; and
   an airflow combination location where the primary and secondary airflows are combined;
   wherein the device for detecting the presence of airborne particulate matter is tested by positioning it operatively with respect to the combined primary and secondary airflows so that it can detect the airborne particulate matter that was originally released into the secondary airflow.

2. The system of 1, wherein said apparatus for measuring the amount of airborne particulate matter released into the secondary airflow comprises an optical particle counter.

3. The system of claim 1, wherein said a particulate aerosol generator comprises:
   a particulate container;
   particulate flow conduit connected to said container and having a terminal end within the secondary airflow;
   a source of gas under pressure, said source being in communication with said container and said particulate flow conduit to generate gas flow in said conduit in which particulate matter from the container is entrained; and
   valve constructed and arranged to control flow of gas through said particulate flow conduit.

4. The system of claim 3, wherein said particulate aerosol generator further comprises a variably-sized orifice in a portion of said particulate flow conduit.

5. The system of claim 3, wherein said valve comprises an electronically controlled valve.

6. The system of claim 3, wherein said source of gas under pressure comprises a vessel containing a compressed inert gas.

7. The system of claim 6, wherein the inert gas is selected from the group consisting essentially of nitrogen, argon, and neon.

8. A method for testing a device for detecting the presence of airborne particulate matter comprising:
   generating a first airflow;
   generating a second airflow;
   filtering the second airflow to remove ambient particulate matter from the second airflow;
   generating an aerosol of particulate material to be detected by the device for detecting; and
   injecting the aerosol into the filtered second airflow;
   quantifying the particulate material injected into the second airflow of air;
   combining the first and second airflows to create a combined airflow; and
   measuring the combined airflow with the device for detecting to be tested.

9. The method of claim 8, further comprising introducing other interferent substances that may be present in the intended operational environment into the first airflow.

10. The method of claim 8, wherein the first airflow is generated so as to simulate ambient conditions in which the device for detecting is intended to be used.

11. The method of claim 8, wherein generating an aerosol comprises:
    directing a gas flow relative to a source of particulate matter so as to entrain a portion of the particulate matter in the gas flow;
    transmitting the gas flow with particulate matter entrained therein through a conduit terminating within the second airflow; and
    controlling the gas flow via a valve so as to control the amount of entrained particulate matter released into the second airflow.

12. The method of claim 8, wherein measuring the particulate material injected into the second airflow of air comprises sampling the second airflow by collecting an amount of the second airflow and directing the collected amount into an optical particle counter.

13. A system for testing a device for detecting the presence of airborne particulate matter comprising:
    means for generating a primary airflow;
    means for generating a secondary airflow;
    filter means operatively positioned with respect to the secondary airflow to remove ambient particulate matter from the secondary airflow;
    a particulate aerosol generating means for generating an amount of airborne particulate matter and for releasing the generated airborne particulate matter into the filtered secondary airflow;
    particulate measuring means for measuring the amount of airborne particulate matter released into the secondary airflow; and
    means for combining the primary and secondary airflows;
    wherein the device for detecting the presence of airborne particulate matter is tested by positioning it operatively with respect to the combined primary and secondary airflows so that it can detect the airborne particulate matter that was released into the secondary airflow.

* * * * *